United States Patent [19]

Maresca

[11] Patent Number: 4,652,820
[45] Date of Patent: Mar. 24, 1987

[54] COMBINED POSITION SENSOR AND MAGNETIC MOTOR OR BEARING

[75] Inventor: Robert L. Maresca, Ossining, N.Y.

[73] Assignee: North American Philips Corporation, New York, N.Y.

[21] Appl. No.: 478,171

[22] Filed: Mar. 23, 1983

[51] Int. Cl.⁴ .................... G01B 7/14; G01N 27/72; F16C 35/00; G01R 33/12

[52] U.S. Cl. .................... 324/207; 324/232; 310/90.5

[58] Field of Search ............... 324/207, 208, 232, 225; 361/143; 308/10; 104/284; 318/652, 653

[56] References Cited

U.S. PATENT DOCUMENTS

| | | | |
|---|---|---|---|
| 3,155,937 | 11/1964 | Kinsey et al. | 361/143 |
| 3,316,516 | 4/1967 | Condon et al. | 336/132 |
| 3,742,409 | 6/1973 | Santis et al. | 324/207 |
| 3,968,753 | 7/1976 | Breitling | 104/284 |
| 4,092,867 | 6/1978 | Matzuk | 73/609 |

FOREIGN PATENT DOCUMENTS 7208753 6/1972 Fed. Rep. of Germany .
1218976 5/1960 France .

Primary Examiner—Ernest F. Karlsen
Assistant Examiner—Walter E. Snow
Attorney, Agent, or Firm—Marc D. Schechter

[57] ABSTRACT

A combined magnetic sensor and actuator device for applying a magnetic force to a magnetizable body and for sensing the distance between the device and the magnetizable body. The device includes a magnetizable pole piece separated from the magnetizable body by gaps. The pole piece, gaps, and magnetizable body form a magnetic circuit with the gaps preferably being the major reluctance of the circuit. Separate means are provided for generating a relatively large time-varying magnetic actuating flux in the magnetic circuit and for generating a relatively small time-varying magnetic sensing flux in the magnetic circuit. Each magnetic flux follows a flux path, such that the two flux paths have at least a portion in common. Detection means measure the relatively small magnetic flux in the magnetic circuit, and thereby measure the distance between the device and the magnetizable body.

19 Claims, 4 Drawing Figures

COMBINED POSITION SENSOR AND MAGNETIC MOTOR OR BEARING

The Government has rights in this invention pursuant to Contract MDA-903-81-C-0529 awarded by the Department of the Army.

BACKGROUND OF THE INVENTION

The invention relates to magnetic actuators and magnetic position sensors. More particularly, the invention relates to magnetic bearings and magnetic reluctance motors, especially those employing feedback control systems.

Magnetic actuators, in the form of magnetic bearings, reluctance motors, and in other forms, have been known for some time. Separately, position sensors have also been known, and in fact have been used in conjunction with magnetic actuators.

U.S. Pat. No. 4,092,867 (Matzuk) discloses, among other things, an ultrasonic scanning apparatus in which an ultrasonic transducer is moved in a predetermined path by magnetic force-generating means. Preferably, servo-control is provided to control the movement of the transducer. The servo-control utilizes a position sensor to determine the position of the transducer in its path. The position signal is compared with a reference signal, representative of the desired position, in order to generate an error signal which is amplified and conditioned to provide a correcting signal which attempts to make the position exactly track the reference.

Particular magnetic force-generating (drive) means disclosed by Matzuk are shown in FIGS. 1–5 and 10–14. In each of these drive means, the driving force is generated by an interaction between the magnetic field of one or more permament magnets and the magnetic field of a current passing through one or more coils.

Position sensors are shown in FIGS. 7, 8, 9, 9a, 12, and 15 of Matzuk. One type of position sensor utilizes a vane element attached to the transducer substrate, a light source, and a light detector. The vane moves between the light source and the light detector, so that the amount of light detected represents the position of the transducer. Another position sensor (FIGS. 9 and 9a) utilize eddy-current vanes attached to the transducer substrate, and coils fixed to the housing, the coils surrounding the vanes. The changing inductance of the coils, due to varying eddy-current losses, indicates the transducer position.

Another position sensor disclosed by Matzuk (FIGS. 12 and 15) utilizes a vane attached to a swinging column. (The transducer is on the free end of the column.) A coil, fixed to the housing, is energized so that the changing inductance of the coil represents the column position and hence also the transducer position.

French Pat. No. 1,218,976 discloses a magnetic position indicator which measures the variation in the inductance of a coil to determine the position of a pilot blade P. A ferrite pole piece is provided with windings and an air gap. It is made part of an LC tuned circuit which is tuned to resonance at an applied frequency. When the blade P is moved into the air gap, the inductance of the coil increases, thereby changing the resonant frequency of the circuit.

The known devices suffer from several disadvantages. First, the separate actuator and position sensor occupy a relatively large volume. With the trend toward miniaturization, this is a problem. It becomes more of a problem when the actuator and sensor are used in, for example, a magnetic bearing on a satellite. Volume and weight are at a premium on satellites.

Second, the actuator and the position sensor present a relatively complex arrangement when combined. In some cases, where both the actuator and the sensor utilize magnetic fields, the arrangement must assure minimal interference between these fields. This may require magnetic shielding.

Third, in magnetic bearings in cryogenic coolers, the actuator and the sensor must be hermetically sealed to the pressure vessel. Separate actuators and sensors therefore require separate hermetic seals. The more hermetic seals used, the higher the cost and the greater likelihood that a failure will occur.

Finally, in some position sensors, notably eddy current sensors, the output signal is strongly temperature-dependent. This can be a problem, especially when the device is used in a harsh environment.

SUMMARY OF THE INVENTION

It is an object of the invention to provide a combined magnetic actuator and position sensor which occupies a relatively small volume.

It is another object of the invention to provide a combined magnetic actuator and position sensor in a relatively simple construction which is relatively inexpensive to manufacture.

It is a further object of the invention to provide a combined magnetic actuator and position sensor in which the position sensor is relatively temperature independent.

According to the invention, a combined magnetic sensor and actuator device is provided for applying a magnetic force to a magnetizable (ferromagnetic) body and for sensing the distance between the device and the magnetizable body. The device comprises a magnetizable pole piece, first and second magnetic flux-generating means, and detection means for measuring magnetic flux. The magnetizable pole piece is separated from the magnetizable body by an air gap. The pole piece, gap, and magnetizable body form a magnetic circuit, with the air gap being the major reluctance of the circuit. The first magnetic flux-generating means generate a relatively large time varying magnetic actuating flux in the magnetic circuit. This magnetic actuating flux follows a first flux path. The second magnetic flux-generating means generates a relatively small time varying magnetic sensing flux in the magnetic circuit. The magnetic sensing flux follows a second flux path having at least a portion in common with the first flux path. The detection means measures the relatively small magnetic sensing flux in the magnetic circuit.

A combined magnetic sensor and actuator device according to the invention is advantageous because it occupies a relatively small volume and because it has a relatively simple construction.

Preferably, in a magnetic sensor and actuator device according to the invention, the first and second flux paths are identical. The first magnetic flux-generating means generates a relatively low frequency magnetic flux, and the second magnetic flux-generating means generates a relatively high frequency magnetic flux. The detection means then measures the high frequency magnetic flux in the magnetic circuit.

The detection means can measure either the amplitude or the phase of the high frequency magnetic flux, either of which is proportional to the distance between the magnetizable pole piece and the magnetizable body.

It is also preferable that the pole piece and the magnetizable body are made of soft-magnetic materials. If a soft-magnetic ferrite is used, eddy-current losses can be minimized.

The geometry of the pole piece is, in one embodiment of the invention, "U"-shaped. In this embodiment, the first and second magnetic flux-generating means comprise a single electrical conductor wound around the pole piece to form a coil.

In another embodiment of the invention, the pole piece is "E"-shaped. In this embodiment, two electrically conducting coils are used.

Preferably, in the magnetic circuit the gaps comprise at least 95% of the total reluctance, in order to provide a highly temperature-stable position sensor.

In all embodiments of the invention, the first and second magnetic flux-generating means preferably comprise means for generating electric currents. The first means generates a relatively low frequency electric current component in the coil and the second means generates a relatively high frequency electric current component in the coil. The detection means then comprises a high-pass filter for separating the high frequency electric current component from the low frequency component. Preferably, the high-pass filter is a notch filter. The detection means also comprises means for measuring either the amplitude or the phase of the high frequency electric current component.

In a preferred embodiment of the invention, the combined magnetic sensor and actuator device further includes negative feedback-control means to minimize the positional error of the magnetizable body.

The magnetic sensor and actuator device according to the invention may be utilized in, for example, magnetic bearings for suspending magnetizable bodies, or in reluctance motors for imparting a desired motion to a magnetizable body.

DESCRIPTION OF THE PREFERRED EMBODIMENTS

Figure 1:
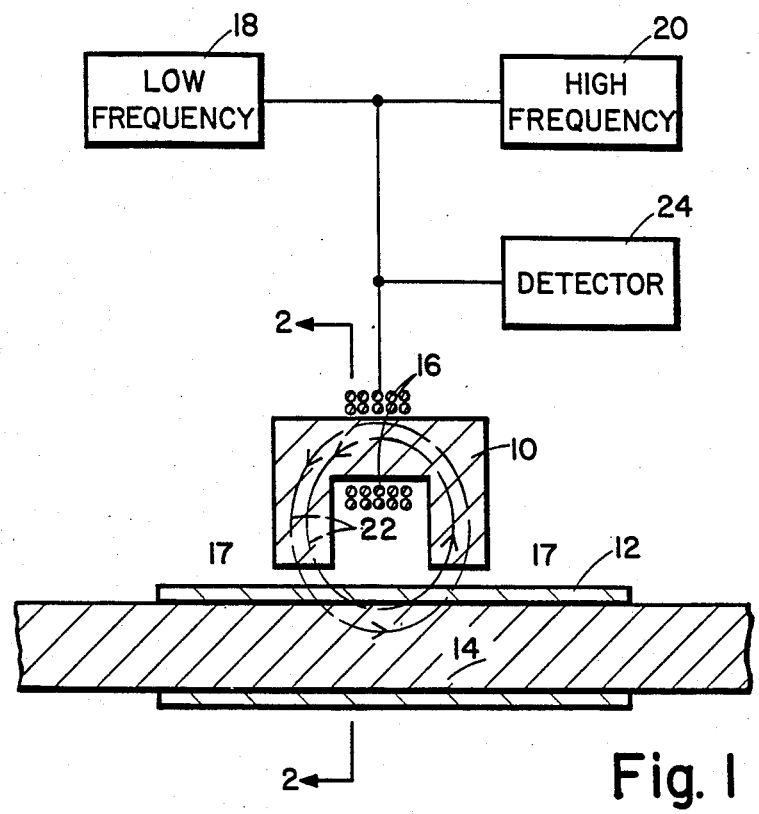
FIG. 1 is a partly schematic, partly cross-sectional view of a combined magnetic sensor and actuator device according to the invention.

FIG. 1 shows a partly schematic, partly cross-sectional view of a combined magnetic position sensor and actuator device according to the invention. The device utilizes a magnetizable pole piece 10 which interacts with a magnetizable body 12. For the purpose of this application, "magnetizable" is meant to be synonymous with "ferromagnetic". In FIG. 1, the magnetizable body 12 is a ferrite sleeve provided on a shaft 14. The magnetizable pole piece 10 is also preferably a ferrite in order to minimize eddy-current losses. Both the magnetizable pole piece and the magnetizable body are preferably soft magnetic materials.

Figure 2:
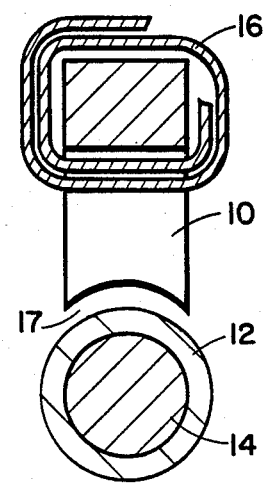
FIG. 2 is a cross-sectional view of a combined magnetic sensor and actuator device according to the invention taken along line II—II of FIG. 1.

Referring now to both FIGS. 1 and 2, it can be seen that the magnetizable pole piece 10 is "U"-shaped. Around the central portion of the "U" an electrical conductor is wound into a coil 16. Coil 16 is powered by a low frequency electric current source 18 and a high frequency electric current source 20. The low frequency electric current passing through coil 16 produces a relatively large magnetic actuating flux in the magnetic circuit. The high frequency electric current flowing through coil 16 produces a relatively small magnetic sensing flux in the magnetic circuit. Both the magnetic actuating flux and the magnetic sensing flux follow flux path 22.

The magnetizable pole piece 10 of FIGS. 1 and 2 has two legs projecting toward the magnetizable body 12. The legs of pole piece 10 are separated from magnetizable body 12 by gaps 17. Pole piece 10, gaps 17, and magnetizable body 12 form a magnetic circuit, with the gaps 17 being the major reluctance of the circuit.

Preferably, gaps 17 are at least 95% of the reluctance of the magnetic circuit. The advantage of this is that the reluctance of the gap will be substantially independent of temperature. Therefore, a measurement of the reluctance of the circuit will indicate the size of the gap (and the distance between pole piece 10 and magnetizable body 12), independent of the temperature at the time of the measurement.

In the operation of the combined magnetic actuator and magnetic sensor shown in FIGS. 1 and 2, the low frequency electric current source 18 provides an actuating signal to the coil 16. In the case of a motor, this signal will be designed to move shaft 14 in a desired manner. In the case of a magnetic bearing, source 18 will supply a current which will tend to maintain shaft 14 at a desired position, opposing any external forces due to applied loads.

High frequency electric current source 20 and detector 24 are utilized to detect the position of shaft 14, as described in more detail below. The position signal generated by detector 24 is then utilized in a feedback loop, also described below, to maintain shaft 14 in its desired trajectory or desired position.

Figure 3:
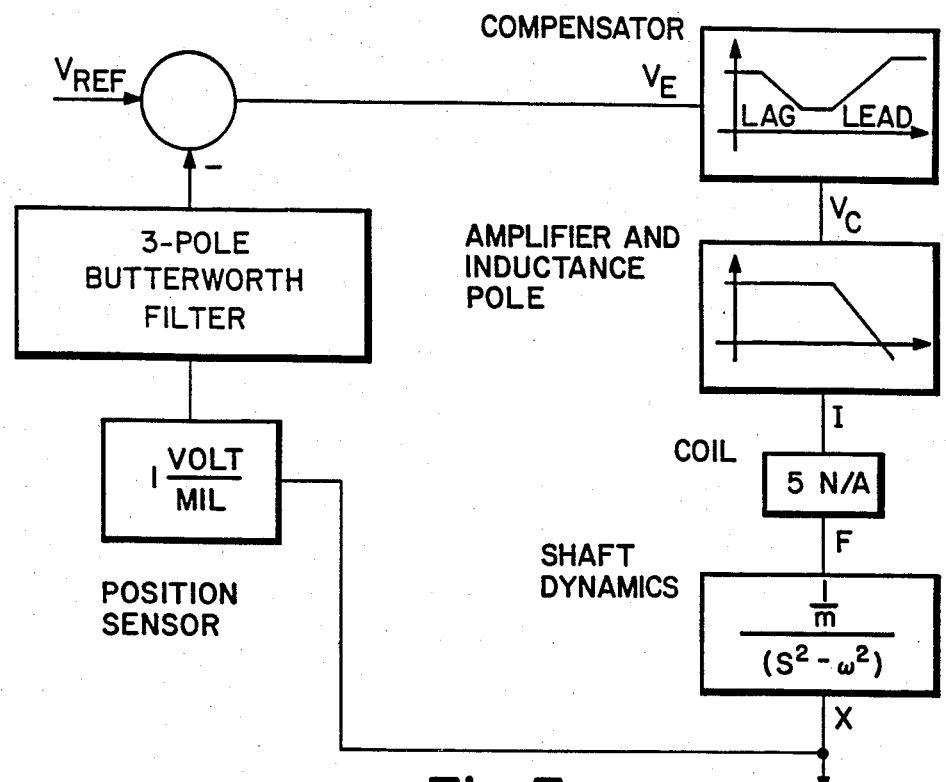
FIG. 3 is a block diagram of a control system for a combined magnetic sensor and actuator device according to the invention.

FIG. 3 is a block diagram of a control system which can be used with the combined magnetic actuator and magnetic sensor of FIGS. 1 and 2. In this system, the shaft position, X, modulates a high frequency carrier signal; this signal is demodulated by passing it through a three-pole Butterworth filter to filter out the high frequency carrier.

The output from the filter is a feedback signal which is next subtracted from a reference signal, $V_{ref}$, to produce an error signal $V_E$. The error signal is passed through a lag-lead compensator, so that the system can be designed to minimize the error signal. The selection of a suitable compensator is a design choice which considers the desired stiffness and the desired damping in the system, as well as system stability requirements.

The compensated signal, $V_C$, is next amplified to drive the actuating coil. An inductance pole is produced by the inductance of the coil. The output of the amplifier, I, is analogous to the current from low frequency source 18 in FIG. 1.

The current passing through the coil produces a force on the magnetizable body. This force, F, is equal to, for example, 5 Newtons per Ampere of coil current. The force is applied to shaft 14 via magnetizable body 12. In accordance with the shaft dynamics (m is the mass of the shaft, and $\omega$ is $\sqrt{k/m}$ where k is the effective spring constant of the system), the force then determines the position, X, of the shaft.

While the control system shown in FIG. 3 is a preferred system, it should be understood that many other control systems can also be designed for use with the combined magnetic actuator and magnetic sensor according to the invention.

Figure 4:
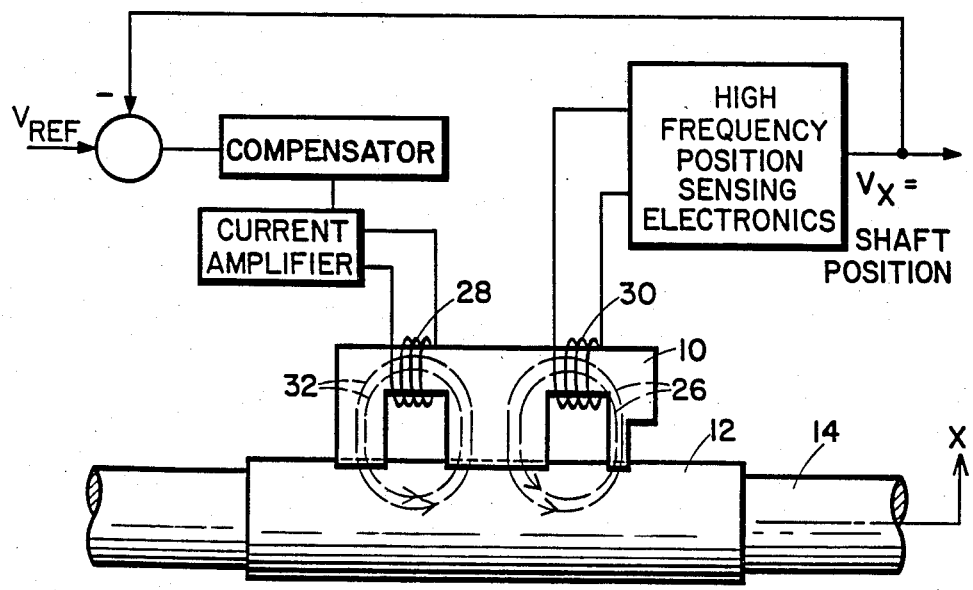
FIG. 4 is a partly schematic, partly perspective view of another embodiment of a combined magnetic sensor and actuator device according to the invention.

FIG. 4 shows an alternate embodiment of a magnetic actuator and magnetic sensor according to the invention. In this embodiment, the combined device is used in a magnetic bearing. While FIG. 4 shows only a single pole piece 10 with a control loop, it should be understood that in practice each end of shaft 14 is usually supported by four such pole pieces with a single control loop for pairs of pole pieces which are radially opposite to each other.

In FIG. 4, pole piece 10 has an E-shaped configuration with three legs. Leg 26 is narrowed down at its end so as to increase the reluctance of this leg. Leg 26 is also shorter than the other two legs of pole piece 10.

The integrated actuator and sensor of FIG. 4 utilizes two coils 28 and 30. Coil 28 functions as a lifting coil and is driven by a current amplifier to provide a low frequency (for example 0 to 1 kilohertz) variable force. Coil 28 is wrapped around a portion of pole piece 10 between the two legs of the pole piece which do not have reduced cross-sectional areas at their ends. This permits the magnetic flux 32, generated by passing a current through coil 28, to travel through a relatively low reluctance circuit to provide maximum flux to the bearing.

Coil 30 functions as a sensing coil and is driven, in operation, by a high frequency (for example, 0.1 to 1 megahertz) oscillator to establish an alternating magnetic flux which is modulated by the position of the shaft. Coil 30 is wound around the portion of pole piece 10 between the center leg and the leg 26. This produces a relatively high reluctance circuit for the magnetic flux generated by passing a current through coil 30. Interference between coils 28 and 30 will be minimized by providing this high reluctance path. Also, the inductance of coil 30 will be highly sensitive to the size of the gap between magnetizable body 12 and the end of leg 26. In this way, the inductance of coil 30 indicates the position of the shaft 14 relative to the pole piece 10.

Preferably, the sensing coil 30 is part of a series resonant LCR circuit (a high-pass notch filter) in which the inductance, L, is a function of the shaft position as follows. First, the reluctance, R, of the magnetic circuit is given by $$R = \frac{X}{\mu_o A} + R_o,$$

where x is the gap thickness, $M_o$ is the permeability of the gap material (essentially a vacuum), A is the cross-sectional area of the pole piece, and $R_o$ is the reluctance of the remainder of the magnetic circuit. Where $$\frac{X}{\mu_o A} >> R_o, R \sim \frac{X}{\mu_o A}.$$

From the reluctance, the inductance of the coil is given by $L = N^2/R$, where N is the number of turns of the coil.

The modulation of the inductance with the shaft position causes a phase shift between the exciting voltage and the resulting current in the coil. This phase shift is converted into a voltage by a demodulator. The functional relationship between the voltage and the shaft position is given by:

$$V_x = A\tan^{-1}[\omega_o RC/(1-\omega_o^2 L(x)C)]$$

where A now equals the amplification factor, $\omega_o$ equals the exciting frequency of the oscillator supplying the resonant LCR circuit, R equals the series resistance, C equals the series capacitance, and L(x) equals the series inductance which is proportional to 1/x. While this function is highly nonlinear, it can be linearized about the desired operating position of the shaft by approximating the slope of the linear function at a point as the first partial derivative of $V_x$ with respect to the position, x. This approximation has been found to be satisfactory for small excursions about this operating point.

It is preferable to measure the phase shift of the voltage across the coil to deduce the position of the shaft, because the resulting signal will have low noise susceptibility. Alternately, however, the position of the shaft could be deduced by measuring the modulated amplitude of the voltage across the coil (or any other element of the LCR circuit).

I claim:

1. A magnetic sensor and actuator device for applying a magnetic force to a magnetizable body and for sensing the distance between the device and the magnetizable body, said device comprising:

a magnetizable pole piece projecting toward the magnetizable body and separated therefrom by gaps, said pole piece, gaps, and magnetizable body forming a magnetic circuit, the gaps being the major reluctance of the magnetic circuit;

first means for generating a relatively large and relatively low frequency time-varying magnetic actuating flux in the magnetic circuit, said flux following a first flux path;

second means for generating a relatively small and relatively high frequency time-varying magnetic sensing flux in the magnetic circuit, said flux following a second flux path having at least a portion in common with the first flux path; and detection mans for measuring the relatively small, relatively high frequency magnetic flux in the magnetic circuit;

characterized in that:

the first magnetic flux-generating means further comprises an electrical conductor wound around the pole piece to form a coil and means for generating a relatively low frequency electric current in the coil, said low frequency electric current being a drive signal;

the second magnetic flux-generating means further comprises an electrical conductor wound around the pole piece to form a coil and means for generating a relatively high frequency electric current in the coil;

the detection means generates a position signal indicating the relative distance between the pole piece and the magnetizable body; and the device further comprises negative feedback-control means which compare a reference signal to the position signal to generate the driving signal.

2. A device as claimed in claim 1, characterized in that the gaps are the major reluctance of the magnetic circuit.

3. A device as claimed in claim 2, characterized in that the first and second flux paths are identical.

4. A device as claimed in claim 3, characterized in that:
   the first magnetic flux-generating means generates a relatively low frequency magnetic flux;
   the second magnetic flux-generating means generates a relatively high frequency magnetic flux; and
   the detection means measures the high frequency magnetic flux in the magnetic circuit.

5. A device as claimed in claim 4, characterized in that the detection means measures the amplitude of the high frequency magnetic flux.

6. A device as claimed in claim 4, characterized in that the detection means measures the phase of the high frequency magnetic flux.

7. A device as claimed in claim 4, characterized in that the pole piece and the magnetizable body are made of soft-magnetic materials.

8. A device as claimed in claim 7, characterized in that the pole piece and the magnetizable body are made of ferrites.

9. A device as claimed in claim 4, characterized in that the pole piece is "U"-shaped.

10. A device as claimed in claim 9, characterized in that the gaps comprise at least 95% of the total reluctance of the magnetic circuit.

11. A device as claimed in claim 10, characterized in that the first and second magnetic flux-generating means comprise a single electrical conductor wound around the pole piece to form a coil.

12. A device as claimed in claim 11, characterized in that:
   the first magnetic flux-generating means further comprises means for generating a relatively low frequency electric current component in the coil; and
   the second magnetic flux-generating means further comprises means for generating a relatively high frequency electric current component in the coil.

13. A device as claimed in claim 12, characterized in that the detection means comprises a high-pass filter for separating the high frequency electric current component from the low frequency component.

14. A device as claimed in claim 13, characterized in that the high-pass filter is a notch filter.

15. A device as claimed in claim 14, characterized in that the detection means further comprises means for measuring the amplitude of the high frequency electric current component.

16. A device as claimed in claim 14, characterized in that the detection means further comprises means for measuring the phase of the high frequency electric current component.

17. A magnetic sensor and actuator device for applying a magnetic force to a magnetizable body and for sensing the distance between the device and the magnetizable body, said device comprising:
   a magnetizable pole piece projecting toward the magnetizable body and separated therefrom by gaps, said pole piece, gaps, and magnetizable body forming a magnetic circuit, the gaps being the major reluctance of the magnetic circuit;
   first means for generating a relatively large and relatively low frequency time-varying magnetic actuating flux in the magnetic circuit, said flux following a first flux path;
   second means for generating a relatively small and relatively high frequency time-varying magnetic sensing flux in the magnetic circuit, said flux following a second flux path having at least a portion in common with the first flux path; and
   detection means for measuring the relatively small, relatively high frequency magnetic flux in the magnetic circuit;
   characterized in that:
   the first and second magnetic flux-generating means comprise a single electrical conductor wound around the pole piece to form a coil;
   the first magnetic flux-generating means further comprises means for generating a relatively low frequency electric current component in the coil, said low frequency electric current component being a drive signal;
   the second magnetic flux-generating means further comprises means for generating a relatively high frequency electric current component in the coil;
   the detection means comprises a high-pass filter for separating the high frequency electric current componet from the low frequency component, said detection means generating a position signal indicating the relative distance between the pole piece and the magnetizable body; and
   the device further comprises negative feedback-control means which compare a reference signal to the position signal to generate the driving signal.

18. A magnetic sensor and actuator devices for applying a magnetic force to a magnetizable body and for sensing the distance between the device and the magnetizable body, said device comprising:
   a magnetizable pole piece projecting toward the magnetizable body and separated therefrom by gaps, said pole piece, gaps, and magnetizable body forming a magnetic circuit, the gaps being the major reluctance of the magnetic circuit;
   first means for generating a relatively large and relatively low frequency time-varying magnetic actuating flux in the magnetic circuit, said flux following a first flux path;
   second means for generating relatively small and relatively high frequency time-varying magnetic sensing flux in the magnetic circuit, said flux following a second flux path having at least a portion in common with the first flux path; and
   detection means for measuring the relatively small, relatively high frequency magnetic flux in the magnetic circuit;
   characterized in that the pole piece has three legs and an "E"-shaped cross-section, one of the legs being shorter than the other two, the shorter leg also having an end with a smaller cross-section than the other two legs.

19. A device as claimed in claim 18, characterized in that the device is a magnetic bearing for suspending the magnetizable body.

* * * * *